(12) United States Patent
Fu

(10) Patent No.: US 12,266,434 B2
(45) Date of Patent: Apr. 1, 2025

(54) SYSTEM AND METHOD FOR INVERSE SUMMARIZATION OF MEDICAL RECORDS WITH DATA AUGMENTATION AND KNOWLEDGE DISTILLATION

(71) Applicant: Microsoft Technology Licensing LLC, Redmond, WA (US)

(72) Inventor: Zhongkai Fu, Bellevue, WA (US)

(73) Assignee: Microsoft Technology Licensing, LLC, Redmond, WA (US)

(*) Notice: Subject to any disclaimer, the term of this patent is extended or adjusted under 35 U.S.C. 154(b) by 288 days.

(21) Appl. No.: 17/951,742

(22) Filed: Sep. 23, 2022

(65) Prior Publication Data
US 2024/0105296 A1  Mar. 28, 2024

(51) Int. Cl.
*G16H 15/00* (2018.01)
*G06F 18/214* (2023.01)
*G06F 40/279* (2020.01)

(52) U.S. Cl.
CPC ......... *G16H 15/00* (2018.01); *G06F 18/2148* (2023.01); *G06F 40/279* (2020.01)

(58) Field of Classification Search
CPC .............................. G06H 15/00; G06F 40/279
See application file for complete search history.

(56) References Cited

U.S. PATENT DOCUMENTS

| | | | |
|---|---|---|---|
| 2020/0334416 A1* | 10/2020 | Vianu | G06V 10/764 |
| 2022/0058507 A1 | 2/2022 | El-Khamy et al. | |
| 2022/0138633 A1 | 5/2022 | Choi et al. | |
| 2023/0046248 A1* | 2/2023 | Veyseh | G06N 3/04 |

FOREIGN PATENT DOCUMENTS

| | | |
|---|---|---|
| CN | 112488944 A | 3/2021 |
| CN | 114780716 A | 3/2022 |
| WO | 2021056046 A1 | 4/2021 |

OTHER PUBLICATIONS

Yang, et al., "UM4: Unified Multilingual Multiple Teacher-Student Model for Zero-Resource Neural Machine Translation", In Repository of arXiv:2207.04900v1, Jul. 11, 2022, 7 Pages.

M. Zhu, J. Li, N. Wang and X. Gao, "Knowledge Distillation for Face Photo-Sketch Synthesis," in IEEE Transactions on Neural Networks and Learning Systems, vol. 33, No. 2, pp. 893-906, Feb. 2022, doi: 10.1109/TNNLS.2020.3030536.

* cited by examiner

*Primary Examiner* — Bryan S Blankenagel
(74) *Attorney, Agent, or Firm* — Brian J. Colandreo; Heath M. Sargeant; Holland & Knight LLP

(57) ABSTRACT

A method, computer program product, and computing system for generating a first synthetic dataset including a synthetic transcription and a corresponding natural dictation record using a first machine learning model trained to generate transcriptions from medical records. A second synthetic dataset including a synthetic medical record and a corresponding natural transcription is generated using a second machine learning model trained to generate medical records from transcriptions. The first synthetic dataset and the second synthetic dataset are combined with a natural dataset into a synthetic training dataset.

17 Claims, 3 Drawing Sheets

SYSTEM AND METHOD FOR INVERSE SUMMARIZATION OF MEDICAL RECORDS WITH DATA AUGMENTATION AND KNOWLEDGE DISTILLATION

BACKGROUND

Medical professional often generate electronic health records (EHRs) from conversations between them and their patients. This process may be performed automatically by using machine learning to generate medical records from transcriptions. However, to effectively train these machine learning models, a significant amount of parallel data (i.e., transcripts and corresponding EHRs) is required. Due to privacy concerns and other legal reasons, these parallel training datasets are scarce in the medical domain.

BRIEF DESCRIPTION OF THE DRAWINGS

Like reference symbols in the various drawings indicate like elements.

DETAILED DESCRIPTION OF THE PREFERRED EMBODIMENTS

As will be discussed in greater detail below, implementations of the present disclosure leverage an existing small-sized dataset to generate synthetic training data for training a machine learning model. Synthetic training data is training data that is artificially created and is not representative of real data (i.e., actual transcriptions and/or medical records). Implementations of the present disclosure use data augmentation to generate large amounts of synthetic training data from the limited existing dataset. For example and as will be discussed in greater detail below, two "teacher" machine learning models are trained on the small-sized dataset to generate a synthetic dataset (e.g., combination of synthetic transcripts and synthetic medical records). The synthetic training dataset is combined with the existing dataset to make a larger training dataset. Implementations of the present disclosure use data augmentation to train a student model (e.g., a summarization model) with the larger training dataset. Accordingly, the accuracy of the student model is enhanced with the increase in the amount of training data available.

The details of one or more implementations are set forth in the accompanying drawings and the description below. Other features and advantages will become apparent from the description, the drawings, and the claims.

Figure 1:
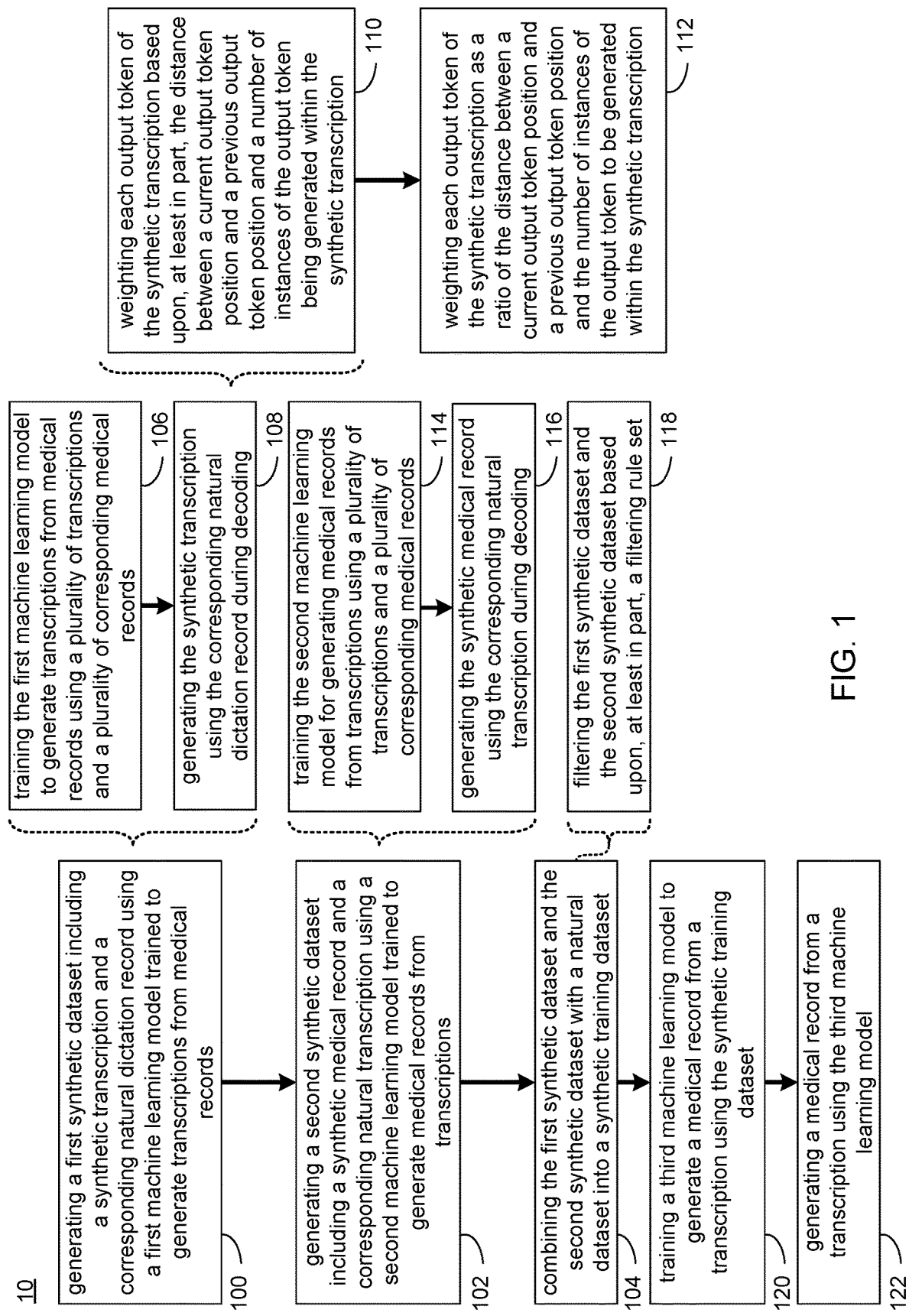
FIG. 1 is a flow chart of one implementation of the training data generation process.
Figure 2:
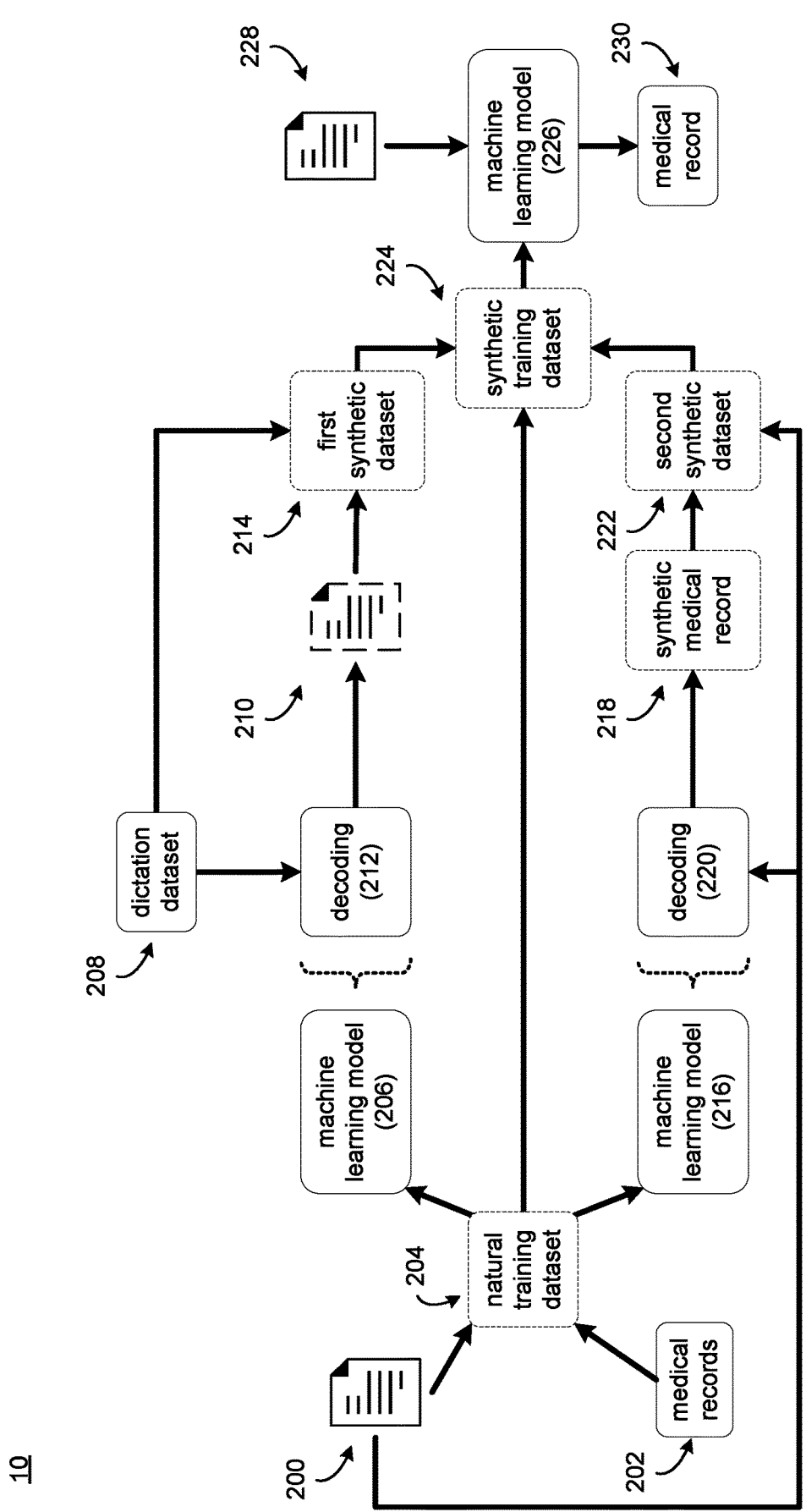
FIG. 2 is a diagrammatic view of the training data generation process.
Figure 3:
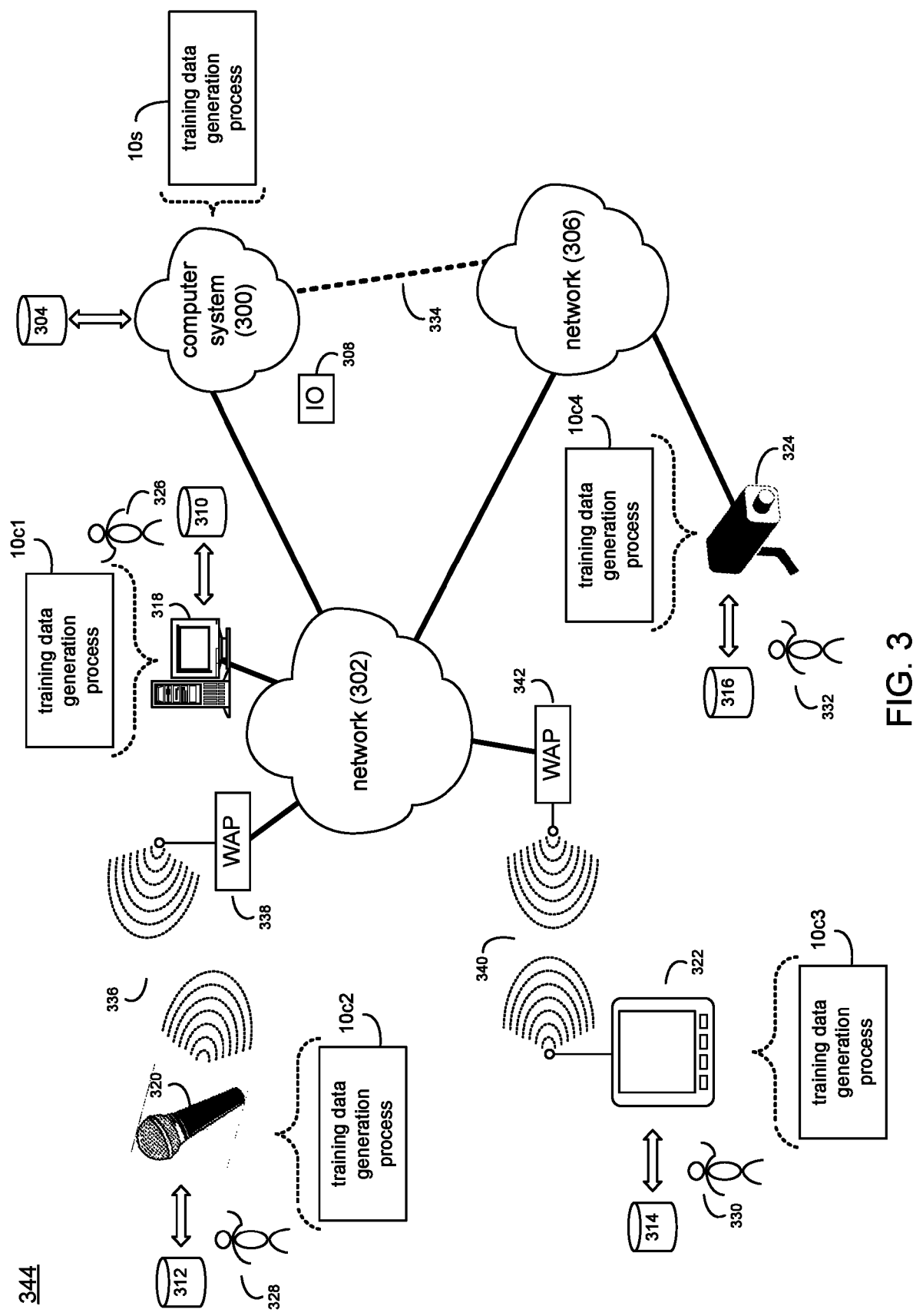
FIG. 3 is a diagrammatic view of a computer system and the training data generation process coupled to a distributed computing network.

The Training Data Generation Process:

Referring also to FIGS. 1-3, training data generation process 10 generates 100 a first synthetic dataset including a synthetic transcription and a corresponding natural dictation record using a first machine learning model trained to generate transcriptions from medical records. A second synthetic dataset including a synthetic medical record and a corresponding natural transcription is generated 102 using a second machine learning model trained to generate medical records from transcriptions. The first synthetic dataset and the second synthetic dataset are combined 104 with a natural dataset into a synthetic training dataset.

As discussed above, the process of automatically generating medical records or electronic health records (EHRs) from transcriptions using machine learning models is limited by the availability of training data for the machine learning model. Additionally, conventional machine learning models used for processing transcriptions are large machine learning models that require significant computing resources. Implementations of the present disclosure provide synthetic training data from a limited set of parallel data (i.e., transcriptions and corresponding medical records) by using data augmentation to generate a larger, synthetic dataset from smaller natural dataset and larger machine learning models and knowledge distillation. Knowledge distillation is the process of transferring the knowledge from a large unwieldy machine learning model or set of machine learning models to a single, smaller machine learning model that can be practically and efficiently deployed under real-world constraints.

As will be described in greater detail below, training data generation process 10 uses one large machine learning model trained to generate transcriptions from medical records in order to generate a first synthetic dataset with a synthetic transcription and a corresponding natural dictation record and another large machine learning model trained to generate medical records from transcriptions in order to generate a second synthetic dataset with a synthetic medical record and a corresponding natural transcription. The first synthetic dataset (i.e., synthetic transcriptions with corresponding natural dictation records) and the second synthetic dataset (i.e., synthetic medical record and a corresponding natural transcription) are combined with the natural dataset (e.g., natural transcriptions and corresponding natural medical records) to define synthetic training data which can be used with the existing small dataset to train a small, student machine learning model to generate medical records from input transcription data. In this manner, the amount of training data available for training a machine learning model to automatically generate medical records from input transcription data is increased. Additionally, the student machine learning model that is deployed is a more efficient (i.e., smaller) machine learning model than conventional machine learning models because of the knowledge distillation from the larger teacher machine learning models. As such, generating medical records from input transcription data using a smaller machine learning model requires fewer computing resources than conventional approaches.

In some implementations, training data generation process 10 generates 100 a first synthetic dataset including a synthetic transcription and a corresponding natural dictation record using a first machine learning model trained to generate transcriptions from medical records. A synthetic transcription is an artificial transcription (i.e., artificial transcription data from an encounter between real or artificial participants). As discussed above, actual or real transcription data may be scarce and/or may include sensitive content (i.e., personally identifiable information, protected health information, financial information, etc.). As such, training data generation process 10 uses a first machine learning model trained to generate transcriptions from medical records in order to generate 100 a first synthetic dataset including synthetic transcriptions with corresponding natural dictation records or medical records.

A machine learning model generally includes an algorithm or combination of algorithms that has been trained to recognize certain types of patterns. For example, machine learning approaches are generally divided into three categories, depending on the nature of the signal available: supervised learning, unsupervised learning, and reinforcement learning. Supervised learning presents a computing device with example inputs and their desired outputs, given by a "teacher", where the goal is to learn a general rule that maps inputs to outputs. With unsupervised learning, no labels are given to the learning algorithm, leaving it on its own to find structure in its input. Unsupervised learning can be a goal in itself (discovering hidden patterns in data) or a means towards an end (feature learning). Reinforcement learning includes a computing device interacting in a dynamic environment in which it must perform a certain goal (such as driving a vehicle or playing a game against an opponent). As it navigates its problem space, the program is provided feedback that's analogous to rewards, which it tries to maximize. While three examples of machine learning approaches have been provided, it will be appreciated that other machine learning approaches are possible within the scope of the present disclosure.

In some implementations, generating 100 the first synthetic dataset includes training 106 the first machine learning model to generate transcriptions from medical records using a plurality of transcriptions and a plurality of corresponding medical records. Training a machine learning model includes providing known inputs and expected outputs in order to train the weighting and organization of the machine learning model to accurately generate the expected outputs for the known inputs. For example and referring also to FIG. 2, suppose training data generation process 10 accesses or receives a plurality of transcriptions (e.g., plurality of transcriptions 200) and a plurality of corresponding medical records (e.g., plurality of medical records 202). In some implementations, plurality of transcriptions 200 and corresponding medical records 202 define a natural training dataset (e.g., natural training dataset 204). In this example, training data generation process 10 provides natural training dataset 204 to a first machine learning model (e.g., first machine learning model 206). Training data generation process 10 trains 106 first machine learning model 206 with natural training dataset 204. In this manner, first machine learning model 206 can generate 100 synthetic transcription data from input medical records. In one example, first machine learning model 206 is a "teacher" machine learning model with a dimension of e.g., 1024, a layer depth of e.g., 6, a vocabulary size of e.g., 60,000, and a multi-head number of e.g., 16. As will be discussed in greater detail below, first machine learning model represents a large machine learning model and is larger than the student machine learning model that is trained to generate medical records from input transcription data.

In some implementations, generating 100 the first synthetic dataset includes generating 108 the synthetic transcription using the corresponding natural dictation record during decoding. A natural dictation record is a record of dictation notes associated with a medical encounter. In one example, a dictation record includes notes dictated (e.g., using a voice recording device) by the medical professional before, during, and/or after an encounter with a patient. In another example, a dictation record includes a summary of an encounter prepared by an individual associated with the encounter. For example, an individual or system may record the interactions between a medical professional and a patient which are transcribed into dictation notes for the encounter. In some implementations, dictation data is generally more abundant and more similar to a transcription than a medical record.

In some implementations, training data generation process 10 preprocesses records of the dictation dataset. For example, training data generation process 10 preprocesses (i.e., before the decoding) the dictation dataset using one or more filtering rules. In one example, the filtering rules indicate that dictation data that is processed includes a sequence starting with the phrase including "year-old" and with a length between e.g., 200 and e.g., 1,000 characters. In another example, the filtering rules specify duplicated tags that are removed during preprocessing of the dictation dataset. The filtering rules are user-defined, default filtering rules, and/or automatically defined by training data generation process 10.

In some implementations, training data generation process 10 generates 108 the synthetic transcription using the corresponding natural dictation record during decoding. Decoding is the process of selecting an output token from a plurality of candidate output tokens when using a trained machine learning model. For example, the operation of a machine learning model that processes medical records to generate transcriptions includes encoding the input medical record into a vector representing that input and decoding the vector to generate a corresponding transcription. In some implementations, encoding and decoding is for each word or phrase of the medical record. During decoding, the machine learning model identifies a plurality of candidate output tokens and determines which output token to select according to various decoding strategies. In one example, training data generation process 10 uses a greedy decoding to select whichever token that is the most probable. In another example, training data generation process 10 uses a beam search strategy by: 1) generating all possible tokens in a vocabulary list at each time step; 2) choosing the top "B" candidates that have the most probability; 3) moving those "B" candidates to the next time step; and 4) repeating the above-described process. In the end, there will only be "B" candidates. In yet another example, training data generation process 10 uses a "top-k" decoding strategy by sampling from a shortlist of the top "k" tokens. This approach allows the other high-scoring tokens a chance of being picked. The randomness introduced by this sampling helps the quality of generation in a lot of scenarios. In yet another example, training data generation process 10 uses the "top-p" decoding strategy which shortlists the top tokens whose sum of likelihoods does not exceed a certain value (e.g., "p"). In this example, training data generation process 10 uses the "top-p" decoding strategy with the following weight decay formula shown as Equation 1:

$$\text{weight}=\text{weight}*N^{(-1.0-y/x)} \tag{1}$$

where N is the hyper-parameter for repeated token penalty with a default value of e.g., 10; y is the number of instances of the token to be generated within the synthetic transcription dataset being processed during decoding, where y>0; and x is the distance between a current position and a previous position of the same token, where x>0. If this is the first time that the token will be generated, the distance is equal to the current position.

In some implementations, Equation 1 only has one hyper-parameter for repeated token penalty, and does not have a hyper-parameter for token distance penalty as is common in conventional decoding strategies. In this manner, the process for tuning first machine learning model 206 is faster than before within only a single hyper-parameter for repeated token penalty.

In some implementations, generating 108 the synthetic transcription using the corresponding natural dictation record during decoding includes weighting 110 each output token of the synthetic transcription based upon, at least in part, the distance between a current output token position and a previous position of this same output token and a number of instances of the output token to be generated within the synthetic transcription. For example, assume that a decoder generates the following text: "[patient] I have left shoulder pain. [doctor] I see. You have." The length of this text is 13 (including all words, punctuations, tags). Suppose that the decoder generates the next token after the second "have". In this example, there is a vocabulary including all tokens that can be generated after the second "have". For the output token "left", its previous position is 4, and the current position of the token to be generated is 14, so the distance would be 10 (e.g., 14−4).

Continuing with this example, the output token "left" could be the next token to be generated, since it is already in the generated text once, so a number of instances of output token "left" within the current synthetic transcription is 2 (i.e., 1+1 where the first "1" represents the token "left" that already appears in the generated text once and the second "1" represents the token "left" that will or would be generated). In another example, the token "symptom" could be the next token to be generated. In this example, since this token has not been generated in the current synthetic transcription yet, the number of instances for the output token "symptom" is "1".

For example and as shown above in Equation 1, training data generation process 10 uses a weight decay formula for each output token that is based upon, at least in part, the distance between a current position and a previous token position and the number of instances of the output token within the synthetic transcription dataset. These penalties in the weighting indicate that a next output token is very unlikely to be a repeat of the previous output token such that repeated output tokens are penalized from being selected as a next output token.

In some implementations, weighting 110 each output token includes weighting 112 each output token as a ratio of the distance between a current output token position and a previous output token position and the number of instances of the output token to be generated within the synthetic transcription dataset. As shown above in Equation 1, training data generation process 10 weights each output token using a ratio of the distance between a current output token position and a previous output token position and the number of instances of the output token within the synthetic transcription dataset. For example, as the distance between successive instances of the output token increases, the penalty applied to that output token decreases. However, if the number of instances of the output token in the synthetic transcription dataset increases, the penalty against that output token increases.

Referring again to FIG. 2, training data generation process 10 generates 100 a synthetic transcription (e.g., synthetic transcription 210) using the trained first machine learning model (e.g., first machine learning model 206) and a natural dictation record from a dictation dataset (e.g., dictation dataset 208) during decoding (e.g., where decoding is represented with block 212 indicative of using the above-described decoding strategies with first machine learning model 206). As discussed above and in some implementations, training data generation process 10 weights 110 each output token of the synthetic transcription based upon, at least in part, the distance between a current output token position and a previous output token position and a number of instances of the output token to be generated within the synthetic transcription dataset.

In one example, suppose a dictation dataset includes the following dictation record:

Example Dictation Record:

55-year-old male presents to the emergency department with significant chest pain, shortness of breath, and nausea. He states his symptoms started intermittently yesterday afternoon. He states the symptoms got much worse just prior to arrival. He states the pain is currently 9/10 in severity and pressure-like in quality. He also states he feels like his heart is racing. He denies any fevers or chills. He denies any productive cough. He denies any syncopal episodes. He denies any lower extremity pain or swelling. He does admit having a pulmonary embolus in 2016.

As shown above, the dictation record includes conversational information associated with an encounter between a medical professional and a patient (i.e., "he states . . . "; "he denies . . . "; and "he . . . admits"). As such, training data generation process 10 uses the conversational information from the dictation dataset to generate 100 the synthetic transcription. For example, suppose that training data generation process 10 uses the dictation record described previously to generate 100 a synthetic transcription. In this example, training data generation process 10 generates the following synthetic transcription:

Corresponding Synthetic Transcription:

_FAMILY_<id>[doctor] next patient's last name is <unk> first name XXX date of birth XXX hey XXX

[patient] hi how are you doing [doctor] I'm good how are you feeling man what's going on

[patient] i don't know just like a pain in my chest and then shortness of breath nausea

[doctor] when did this start

[patient] yesterday afternoon it was really bad but today it's not as bad

[doctor] okay so the symptoms got much worse before you came to see me uh

[patient] yeah

[doctor] what number would you give your pain right now zero to ten

[patient] nine

[doctor] okay and where does it hurt at

[patient] right here

[doctor] all over the place uh any fevers or chills

[patient] no

[doctor] coughing up anything for you bringing up stuff from the lungs

[patient] no

[doctor] have you ever had a pulmonary embolism before

[patient] yes sir

[doctor] when was that done remind me

[patient] two thousand sixteen

[doctor] okay and you're still having some shortness of breath with exertion too

[patient] mm-hmm

[doctor] any leg pain or swelling at all

[patient] no sir

[doctor] okay let me take a listen to you let's get an ekg real quick make sure everything looks okay there and then I'll come back in after we get that done okay

[patient] alright thank you

[doctor] physical exam he appears fatigued. heart rate is regular rhythm without murmurs gallops or rubs. lungs clear to auscultation bilaterally. assessment and plan under chest pain due to atypical presentation likely secondary to pericarditis however given his history of pe, we'll obtain further evaluation by cardiology. if symptoms worsen or change in nature may need cardiac work-up including stress test et cetera. patient understands and agrees to go forward with this plan of care. meanwhile advised supportive care measures reviewed signs symptoms worsening condition including severe chest pain, shortness of breath fever or chills. should these occur should be evaluated immediately prior to seeing us. patient has been instructed on worrisome signs and symptoms to monitor for such as severe chest pain or other concerning complications.

As shown above, the synthetic transcription includes emphasized portions from the dictation record. In this example, training data generation process 10 uses the relevant medical information from the dictation dataset in combination with the trained first machine learning model to generate a synthetic transcription with the relevant medical information. In this manner, training data generation process 10 generates a synthetic transcription from limited input data (e.g., the dictation dataset and/or existing, natural transcription data).

In some implementations, training data generation process 10 generates 100 a first synthetic dataset (e.g., first synthetic dataset 214) with synthetic transcription 210 and corresponding natural dictation record 208. In this manner, first synthetic dataset 214 includes pairs of synthetic transcriptions and corresponding natural dictation records.

In some implementations, training data generation process 10 generates 102 a second synthetic dataset including a synthetic medical record and a corresponding natural transcription using a second machine learning model trained to generate medical records from transcriptions. For example and as discussed above, training data generation process 10 generates synthetic medical record data that corresponds to either "natural"/existing transcriptions or synthetic transcriptions. In this manner, the ability or "knowledge" for generating medical records from transcriptions are distilled or passed from a second machine learning model to a student machine learning model.

In some implementations, generating 102 the second synthetic dataset includes training 114 the second machine learning model for generating medical records from transcriptions using a plurality of transcriptions and a plurality of corresponding medical records. For example and referring again to FIG. 2, suppose training data generation process 10 accesses or receives a plurality of transcriptions (e.g., plurality of transcriptions 200) and a plurality of corresponding medical records (e.g., plurality of medical records 202). As discussed above, plurality of transcriptions 200 and corresponding plurality of medical records 202 define natural training dataset 204. In this example, training data generation process 10 provides natural training dataset 204 to a second machine learning model (e.g., second machine learning model 216). Training data generation process 10 trains 114 second machine learning model 216 with natural training dataset 204. In this manner, second machine learning model 216 can generate 102 synthetic medical records from input transcription data.

In one example, second machine learning model 216 is a "teacher" machine learning model with a dimension of e.g., 1024, a layer depth of e.g., 6, a vocabulary size of e.g., 60,000, and a multi-head number of e.g., 16. However, these are provided only for example purposes as the machine learning models may include various characteristics. In some implementations, first machine learning model 206 and second machine learning model 216 are equivalent (i.e., include the same characteristics in terms of layer depth, dimensions, vocabulary size, etc.). In some implementations, first machine learning model 206 and second machine learning model 216 have distinct characteristics in terms of layer depth, dimensions, vocabulary size, etc. As will be discussed in greater detail below, second machine learning model represents a large machine learning model and is larger than the student machine learning model (e.g., a third machine learning model) that is trained to generate medical records from input transcription data.

In some implementations, generating 102 the second synthetic dataset includes generating 116 the synthetic medical record using the corresponding natural transcription during decoding. For example and as shown in FIG. 2, with trained second machine learning model 216, training data generation process 10 generates 102 a synthetic medical record (e.g., synthetic medical record 218) during decoding (e.g., where decoding is represented with block 220 indicative of using the above-described decoding strategies with second machine learning model 216). As discussed above and in some implementations, training data generation process 10 weights each output token of the synthetic medical record based upon, at least in part, the distance between a current output token position and a previous output token position and a number of instances of the output token within the synthetic medical record (e.g., synthetic medical record 218).

In some implementations, training data generation process 10 combines 104 the first synthetic dataset and the second synthetic dataset with a natural dataset into a synthetic training dataset. For example, training data generation process 10 uses first synthetic dataset 214 (e.g., synthetic transcription dataset 210 and corresponding natural dictation record 208), second synthetic dataset 222 (e.g., synthetic medical record 218 and corresponding natural transcription 200), and natural training dataset 204 to generate new parallel training data (i.e., synthetic transcriptions with corresponding natural dictation records, synthetic medical records with corresponding natural transcriptions, and natural medical records with corresponding natural transcriptions) for a student machine learning model. While FIG. 2 shows natural training dataset 204 being combined with first synthetic dataset 214 and second synthetic dataset 222, any natural dataset may be combined into a synthetic training dataset. In this manner, the combined synthetic training dataset (e.g., synthetic training dataset 224) represents the distilled knowledge and the augmented data from first machine learning model 206 and second machine learning model 216 for generating medical records from transcriptions.

In some implementations, combining 104 the first synthetic dataset and the second synthetic dataset into a synthetic training dataset includes filtering 118 the first synthetic dataset and the second synthetic dataset based upon, at least in part, a filtering rule set. For example, training data generation process 10 applies a filtering rule set to filter out low quality synthetic transcripts and synthetic medical records. The filtering rule set includes user-defined filtering rules, default filtering rules, and/or filtering rules defined automatically by training data generation process 10. In one example, training data generation process 10 determines whether a sequence is repeated two or more times in 8 grams. If a repeated sequences is identified more than twice, the synthetic transcript and corresponding synthetic medical record pair are filtered out. In another example, if an unknown output token occurs more than e.g., four times, the synthetic transcription and corresponding synthetic medical record are filtered out. In another example, if the length of synthetic text is less than e.g., 200 characters, the synthetic transcription and corresponding synthetic medical record are filtered out. In yet another example, if corresponding pairs of tags are not identified, the synthetic transcription and corresponding synthetic medical record are filter out. For example, suppose that a synthetic transcription includes a "<DATE>" tag, but no corresponding "</DATE>" tag. In this example, training data generation process 10 filters the synthetic transcription and corresponding synthetic medical record from the synthetic training dataset. As discussed above, various filtering rules may be applied for particular datasets.

In some implementations, training data generation process 10 trains 120 a third machine learning model to generate a medical record from a transcription using the synthetic training dataset. For example and as discussed above, training data generation process 10 uses first machine learning model 206 and second machine learning model 216 to generate synthetic training dataset 224. Synthetic training dataset 224 distills the "knowledge" of trained first machine learning model 206 and trained second machine learning model 216 into the third machine learning model (e.g., third machine learning model 226). In this manner, third machine learning model 226 is a student machine learning model to the teacher machine learning models of first machine learning model 206 and second machine learning model 216. For example, when trained with synthetic training dataset 224, third machine learning model 226 benefits from the knowledge of each teach machine learning model while being a smaller and more computationally efficient machine learning model.

In some implementations, training data generation process 10 generates 122 a medical record from a transcription using the third machine learning model. For example, once trained, third machine learning model 226 is able to process transcriptions (e.g., transcription 228) to generate a medical record (e.g., medical record 230). In some implementations, third machine learning model 226 is a smaller machine learning model than conventional machine learning models used for processing transcriptions. Accordingly, third machine learning model 226 is able to more efficiently process transcriptions to generate medical records than conventional machine learning models by using data augmentation and knowledge distilled from first machine learning model 206 and second machine learning model 216.

System Overview:

Referring to FIG. 3, there is shown training data generation process 10. Training data generation process 10 may be implemented as a server-side process, a client-side process, or a hybrid server-side/client-side process. For example, training data generation process 10 may be implemented as a purely server-side process via training data generation process 10s. Alternatively, training data generation process 10 may be implemented as a purely client-side process via one or more of training data generation process 10c1, training data generation process 10c2, training data generation process 10c3, and training data generation process 10c4. Alternatively still, training data generation process 10 may be implemented as a hybrid server-side/client-side process via training data generation process 10s in combination with one or more of training data generation process 10c1, training data generation process 10c2, training data generation process 10c3, and training data generation process 10c4.

Accordingly, training data generation process 10 as used in this disclosure may include any combination of training data generation process 10s, training data generation process 10c1, training data generation process 10c2, training data generation process 10c3, and training data generation process 10c4.

Training data generation process 10s may be a server application and may reside on and may be executed by a computer system 300, which may be connected to network 302 (e.g., the Internet or a local area network). Computer system 300 may include various components, examples of which may include but are not limited to: a personal computer, a server computer, a series of server computers, a mini computer, a mainframe computer, one or more Network Attached Storage (NAS) systems, one or more Storage Area Network (SAN) systems, one or more Platform as a Service (PaaS) systems, one or more Infrastructure as a Service (IaaS) systems, one or more Software as a Service (SaaS) systems, a cloud-based computational system, and a cloud-based storage platform.

A SAN includes one or more of a personal computer, a server computer, a series of server computers, a mini computer, a mainframe computer, a RAID device and a NAS system. The various components of computer system 300 may execute one or more operating systems.

The instruction sets and subroutines of training data generation process 10s, which may be stored on storage device 304 coupled to computer system 300, may be executed by one or more processors (not shown) and one or more memory architectures (not shown) included within computer system 300. Examples of storage device 304 may include but are not limited to: a hard disk drive; a RAID device; a random access memory (RAM); a read-only memory (ROM); and all forms of flash memory storage devices.

Network 302 may be connected to one or more secondary networks (e.g., network 306), examples of which may include but are not limited to: a local area network; a wide area network; or an intranet, for example.

Various IO requests (e.g., IO request 308) may be sent from training data generation process 10s, training data generation process 10c1, training data generation process 10c2, training data generation process 10c3 and/or training data generation process 10c4 to computer system 300. Examples of IO request 308 may include but are not limited to data write requests (i.e., a request that content be written to computer system 300) and data read requests (i.e., a request that content be read from computer system 300).

The instruction sets and subroutines of training data generation process 10c1, training data generation process 10c2, training data generation process 10c3 and/or training data generation process 10c4, which may be stored on storage devices 310, 312, 314, 316 (respectively) coupled to client electronic devices 318, 320, 322, 324 (respectively), may be executed by one or more processors (not shown) and one or more memory architectures (not shown) incorporated into client electronic devices 318, 320, 322, 324 (respectively). Storage devices 310, 312, 314, 316 may include but are not limited to: hard disk drives; optical drives; RAID devices; random access memories (RAM); read-only memories (ROM), and all forms of flash memory storage devices. Examples of client electronic devices 318, 320, 322, 324 may include, but are not limited to, personal computing device 318 (e.g., a smart phone, a personal digital assistant, a laptop computer, a notebook computer, and a desktop computer), audio input device 320 (e.g., a handheld microphone, a lapel microphone, an embedded microphone (such as those embedded within eyeglasses, smart phones, tablet computers and/or watches) and an audio recording device), display device 322 (e.g., a tablet computer, a computer monitor, and a smart television), machine vision input device 324 (e.g., an RGB imaging system, an infrared imaging system, an ultraviolet imaging system, a laser imaging system, a SONAR imaging system, a RADAR imaging system, and a thermal imaging system), a hybrid device (e.g., a single device that includes the functionality of one or more of the above-references devices; not shown), an audio rendering device (e.g., a speaker system, a headphone system, or an earbud system; not shown), various medical devices (e.g., medical imaging equipment, heart monitoring machines, body weight scales, body temperature thermometers, and blood pressure machines; not shown), and a dedicated network device (not shown).

Users 326, 328, 330, 332 may access computer system 300 directly through network 302 or through secondary network 306. Further, computer system 300 may be connected to network 302 through secondary network 306, as illustrated with link line 334.

The various client electronic devices (e.g., client electronic devices 318, 320, 322, 324) may be directly or indirectly coupled to network 302 (or network 306). For example, personal computing device 318 is shown directly coupled to network 302 via a hardwired network connection. Further, machine vision input device 324 is shown directly coupled to network 306 via a hardwired network connection. Audio input device 320 is shown wirelessly coupled to network 302 via wireless communication channel 336 established between audio input device 320 and wireless access point (i.e., WAP) 338, which is shown directly coupled to network 302. WAP 338 may be, for example, an IEEE 802.11a, 802.11b, 802.11g, 802.11n, Wi-Fi, and/or Bluetooth™ device that is capable of establishing wireless communication channel 336 between audio input device 320 and WAP 338. Display device 322 is shown wirelessly coupled to network 302 via wireless communication channel 340 established between display device 322 and WAP 342, which is shown directly coupled to network 302.

The various client electronic devices (e.g., client electronic devices 318, 320, 322, 324) may each execute an operating system, wherein the combination of the various client electronic devices (e.g., client electronic devices 318, 320, 322, 324) and computer system 300 may form modular system 344.

General:

As will be appreciated by one skilled in the art, the present disclosure may be embodied as a method, a system, or a computer program product. Accordingly, the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present disclosure may take the form of a computer program product on a computer-usable storage medium having computer-usable program code embodied in the medium.

Any suitable computer usable or computer readable medium may be used. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, or a magnetic storage device. The computer-usable or computer-readable medium may also be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to the Internet, wireline, optical fiber cable, RF, etc.

Computer program code for carrying out operations of the present disclosure may be written in an object-oriented programming language. However, the computer program code for carrying out operations of the present disclosure may also be written in conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network/a wide area network/the Internet.

The present disclosure is described with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, may be implemented by computer program instructions. These computer program instructions may be provided to a processor of a general-purpose computer/special purpose computer/other programmable data processing apparatus, such that the instructions, which execute via the processor of the computer or other programmable data processing apparatus, create means for implementing the functions/acts specified in the flowchart and/or block diagram block or blocks.

These computer program instructions may also be stored in a computer-readable memory that may direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

The flowcharts and block diagrams in the figures may illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function (s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, not at all, or in any combination with any other flowcharts depending upon the functionality involved. It will also be noted that each block of the block diagrams and/or flowchart illustrations, and combinations of blocks in the block diagrams and/or flowchart illustrations, may be implemented by special purpose hardware-based systems that perform the specified functions or acts, or combinations of special purpose hardware and computer instructions.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

A number of implementations have been described. Having thus described the disclosure of the present application in detail and by reference to embodiments thereof, it will be apparent that modifications and variations are possible without departing from the scope of the disclosure defined in the appended claims.

What is claimed is:

1. A computer-implemented method, executed on a computing device, comprising:
    generating a first synthetic dataset including a synthetic transcription and a corresponding natural dictation record using a first machine learning model trained to generate transcriptions from medical records;
    generating a second synthetic dataset including a synthetic medical record and a corresponding natural transcription using a second machine learning model trained to generate medical records from transcriptions;
    combining the first synthetic dataset and the second synthetic dataset with a natural dataset into a synthetic training dataset;
    training a third machine learning model to generate a medical record from a transcription using the synthetic training dataset by knowledge distillation from the first machine learning model and the second machine learning model to the third machine learning model for generating the synthetic medical record from the transcriptions, wherein the third machine learning model is smaller than the first machine learning model and the second machine learning model; and
    generating a medical record from a transcription using the third machine learning model.

2. The computer-implemented method of claim 1, wherein generating the first synthetic dataset includes:
    training the first machine learning model to generate transcriptions from medical records using a plurality of transcriptions and a plurality of corresponding medical records.

3. The computer-implemented method of claim 1, wherein generating the first synthetic dataset includes:
    generating the synthetic transcription using the corresponding natural dictation record during decoding.

4. The computer-implemented method of claim 3, wherein generating the synthetic transcription using the corresponding natural dictation record during decoding includes:
    weighting each output token of the synthetic transcription based upon, at least in part, the distance between a current output token position and a previous output token position and a number of instances of the output token being generated within the synthetic transcription.

5. The computer-implemented method of claim 1, wherein generating the second synthetic dataset includes:
    training the second machine learning model for generating medical records from transcriptions using a plurality of transcriptions and a plurality of corresponding medical records.

6. The computer-implemented method of claim 1, wherein combining the first synthetic dataset and the second synthetic dataset with the natural dataset into the synthetic training dataset includes:
    filtering the first synthetic dataset and the second synthetic dataset based upon, at least in part, a filtering rule set.

7. A computing system comprising:
    a memory; and
    a processor to perform operations comprising:
    generating a first synthetic dataset including a synthetic transcription and a corresponding natural dictation record using a first machine learning model trained to generate transcriptions from medical records;
    generating a second synthetic dataset including a synthetic medical record and a corresponding natural transcription using a second machine learning model trained to generate medical records from transcriptions;
    combining the first synthetic dataset and the second synthetic dataset with a natural dataset into a synthetic training dataset, and;
    training a third machine learning model to generate medical records using the synthetic training dataset by knowledge distillation from the first machine learning model and the second machine learning model to the third machine learning model for generating the synthetic medical record from the transcriptions, wherein the third machine learning model is smaller than the first machine learning model and the second machine learning model; and
generating a medical record from a transcription using the third machine learning model.

8. The computing system of claim 7, wherein generating the first synthetic dataset includes:
training the first machine learning model to generate transcriptions from medical records using a plurality of transcriptions and a plurality of corresponding medical records.

9. The computing system of claim 7, wherein generating the first synthetic dataset includes:
generating the synthetic transcription using the corresponding natural dictation record during decoding.

10. The computing system of claim 9, wherein generating the synthetic transcription using the corresponding natural dictation record during decoding includes:
weighting each output token of the synthetic transcription based upon, at least in part, the distance between a current output token position and a previous output token position and a number of instances of the output token being generated within the synthetic transcription.

11. The computing system of claim 7, wherein generating the second synthetic dataset includes:
training the second machine learning model for generating medical records from transcriptions using a plurality of transcriptions and a plurality of corresponding medical records.

12. The computing system of claim 7, wherein generating the synthetic medical record includes:
generating the synthetic medical record using the corresponding natural transcription during decoding.

13. A computer program product residing on a non-transitory computer readable medium having a plurality of instructions stored there on which, when executed by a processor, cause the processor to perform operations comprising:
generating a first synthetic dataset including a synthetic transcription and a corresponding natural dictation record during decoding using a first machine learning model trained to generate transcriptions from medical records, wherein generating the first synthetic dataset during decoding includes weighting each output token of the synthetic transcription based upon, at least in part, the distance between a current output token position and a previous output token position and a number of instances of the output token to be generated within the synthetic transcription;
generating a second synthetic dataset including a synthetic medical record and a corresponding natural transcription using a second machine learning model trained to generate medical records from transcriptions;
combining the first synthetic dataset and the second synthetic dataset with a natural dataset into a synthetic training dataset;
training a third machine learning model to generate a medical record from a transcription using the synthetic training dataset by knowledge distillation from the first machine learning model and the second machine learning model to the third machine learning model for generating the synthetic medical record from the transcriptions, wherein the third machine learning model is smaller than the first machine learning model and the second machine learning model; and
generating a medical record from a transcription using the third machine learning model.

14. The computer program product of claim 13, wherein generating the first synthetic dataset includes:
training the first machine learning model to generate transcriptions from medical records using a plurality of transcriptions and a plurality of corresponding medical records.

15. The computer program product of claim 13, wherein weighting each output token of the synthetic transcription includes:
weighting each output token of the synthetic transcription as a ratio of the distance between a current output token position and a previous output token position and the number of instances of the output token to be generated within the synthetic transcription.

16. The computer program product of claim 13, wherein generating the second synthetic dataset includes:
training the second machine learning model for generating medical records from transcriptions using a plurality of transcriptions and a plurality of corresponding medical records.

17. The computer program product of claim 13, wherein combining the first synthetic dataset and the second synthetic dataset with the natural dataset into the synthetic training dataset includes:
filtering the first synthetic dataset and the second synthetic dataset based upon, at least in part, a filtering rule set.

* * * * *